(12) United States Patent
Goos et al.

(10) Patent No.: US 12,083,045 B2
(45) Date of Patent: Sep. 10, 2024

(54) CALIBRATING THE POSITION OF THE FOCAL POINT OF A LASER BEAM

(71) Applicant: Alcon Inc., Fribourg (CH)

(72) Inventors: Evi Goos, Heroldsbach (DE); Claudia Gorschboth, Nuremberg (DE); Matthias Foesel, Memmelsdorf (DE); Olaf Kittelmann, Berlin (DE)

(73) Assignee: ALCON INC., Fribourg (CH)

( * ) Notice: Subject to any disclaimer, the term of this patent is extended or adjusted under 35 U.S.C. 154(b) by 1101 days.

(21) Appl. No.: 16/785,046

(22) Filed: Feb. 7, 2020

(65) Prior Publication Data

US 2020/0266601 A1    Aug. 20, 2020

Related U.S. Application Data

(60) Provisional application No. 62/807,593, filed on Feb. 19, 2019.

(51) Int. Cl.
*A61F 9/008* (2006.01)
*B23K 26/04* (2014.01)
(Continued)

(52) U.S. Cl.
CPC ............... *A61F 9/008* (2013.01); *B23K 26/04* (2013.01); *B23K 26/064* (2015.10);
(Continued)

(58) Field of Classification Search
CPC .................. B23K 26/04; B23K 26/064; A61F 2009/00855; A61F 2009/00897;
(Continued)

(56) References Cited

U.S. PATENT DOCUMENTS 5,162,641 A * 11/1992 Fountain ............... G02B 7/32
351/221
5,841,125 A * 11/1998 Livingston ............ G01J 9/02
356/450

(Continued)

FOREIGN PATENT DOCUMENTS

CN          1067573 A    1/1993
CN       101616647 A   12/2009
(Continued)

*Primary Examiner* — Dani Fox
*Assistant Examiner* — Soorena Kefayati

(57) ABSTRACT

In certain embodiments, a system for calibrating the focal point of a laser beam comprises a laser, focusing optics, detector optics, a two-photon absorption (TPA) detector, and a computer. The laser generates the laser beam. The focusing optics direct the focal point of the laser beam along a z-axis towards a zero-surface corresponding to a zero-plane, and receives a portion of the laser beam reflected by the zero-surface. The detector optics receive the reflected portion from the focusing optics, and directs the reflected portion towards a TPA detector. The TPA detector senses the peak intensity of the reflected portion, which indicates a proximity of the focal point to the zero-surface, and generates a signal representing the peak intensity of the reflected portion. The computer determines whether the focal point of the laser beam is calibrated in response to the signal representing the peak intensity.

15 Claims, 4 Drawing Sheets

(51) Int. Cl.
*B23K 26/064* (2014.01)
*G02B 5/30* (2006.01)
*H01S 3/10* (2006.01)

(52) U.S. Cl.
CPC .............................. *H01S 3/10053* (2013.01);
*A61F 2009/00855* (2013.01); *G02B 5/3083* (2013.01)

(58) Field of Classification Search
CPC . A61F 9/008; G01J 1/4257; G01J 2001/4261; G02B 5/3083; G02B 26/0825; G02B 26/105; G02B 27/0983; G02B 27/286; G02B 27/30; A61B 2018/20359; A61B 2018/20553; A61B 2018/205547; H01S 3/101; H01S 3/10053
See application file for complete search history.

(56) References Cited

U.S. PATENT DOCUMENTS

| | | | | |
|---|---|---|---|---|
| 2003/0206288 | A1* | 11/2003 | Tabirian | G01J 1/4257 356/121 |
| 2007/0123845 | A1* | 5/2007 | Lubatschowski | A61F 9/00825 606/5 |
| 2011/0176402 | A1 | 7/2011 | Higuchi | |
| 2011/0193269 | A1* | 8/2011 | Ito | G02B 21/0032 264/400 |
| 2011/0317153 | A1* | 12/2011 | Holmberg | G01J 1/4257 356/122 |
| 2012/0083771 | A1* | 4/2012 | Warm | A61F 9/00836 606/4 |
| 2012/0268647 | A1* | 10/2012 | Nakagawa | H04N 23/673 348/E5.045 |
| 2013/0183833 | A1* | 7/2013 | Duan | B23K 26/0676 219/121.73 |
| 2014/0316389 | A1* | 10/2014 | Schuele | A61F 9/00825 606/5 |
| 2015/0282988 | A1* | 10/2015 | Simoneau | A61B 90/361 606/5 |
| 2017/0063025 | A1* | 3/2017 | Wakabayashi | H01S 3/1394 |
| 2018/0256391 | A1* | 9/2018 | Vogler | A61F 9/0084 |
| 2021/0003445 | A1* | 1/2021 | Blázquez-Sánchez | B23K 26/707 |

FOREIGN PATENT DOCUMENTS

| | | |
|---|---|---|
| CN | 101981437 A | 2/2011 |
| CN | 102597841 A | 7/2012 |
| CN | 102761704 A | 10/2012 |
| JP | 2006198634 A | 8/2006 |
| WO | 2008055506 A2 | 5/2008 |
| WO | 2009123359 A1 | 10/2009 |
| WO | 2011059679 A1 | 5/2011 |
| WO | 2014158615 A1 | 10/2014 |

\* cited by examiner

CALIBRATING THE POSITION OF THE FOCAL POINT OF A LASER BEAM

TECHNICAL FIELD

The present disclosure relates generally to laser devices, e.g., as used in surgical devices, and more specifically to calibrating the position of the focal point of a laser beam.

BACKGROUND

In ophthalmological laser surgery, making precise cuts is important. For example, a laser assisted in-situ keratomileusis (LASIK) flap is typically created sufficiently near the Bowman's layer to avoid trauma caused by pulling back the flap, but sufficiently far from the Bowman's layer to avoid breaching the layer, so the flap is cut to a depth of approximately 80 micrometers ($\mu$m) to 500 $\mu$m, such as approximately 120 $\mu$m. As another example, the lenticule removed in a SMall Incision Lenticule Extraction (SMILE) procedure leaves the cornea with a curvature that is intended to provide refractive correction, so the lenticule must be precisely cut. Accordingly, to enable consistent, high-quality results, the focal point position of the laser beam should be calibrated within a precision of a few micrometers.

BRIEF SUMMARY

In certain embodiments, a system for calibrating the position of the focal point of a laser beam comprises a laser, focusing optics, detector optics, a two-photon absorption (TPA) detector, and a computer. The laser generates the laser beam. The focusing optics direct the laser beam along a z-axis towards a zero-surface corresponding to a zero-plane, and receive a portion of the laser beam reflected by the zero-surface. The detector optics receive the reflected portion from the focusing optics, and direct the reflected portion towards a TPA detector. The TPA detector senses the peak intensity of the reflected portion, which indicates a proximity of the position of the focal point to the zero-surface, and generates a signal representing the peak intensity of the reflected portion. The computer determines whether the position of the focal point of the laser beam is calibrated in response to the signal representing the peak intensity.

In certain embodiments, a method for calibrating the position of the focal point of a laser beam comprises generating the laser beam. The laser beam is directed by focusing optics along a z-axis towards a zero-surface corresponding to a zero-plane, which reflects at least a portion of the laser beam. The reflected portion is received at the focusing optics and then by detector optics from the focusing optics. The reflected portion is directed towards a two-photon absorption (TPA) detector. The peak intensity of the reflected portion is sensed by the TPA detector. The peak intensity indicates a proximity of the focal point to the zero-surface. A signal representing the peak intensity of the reflected portion is generated. Whether the position of the focal point of the laser beam is calibrated is determined by a computer in response to the signal representing the peak intensity.

Embodiments of the systems and methods may include one, two, or more of any of the following features:

The computer determines whether the peak intensity is a maximum peak intensity. If the peak intensity is the maximum peak intensity, the computer determines that the focal point is substantially at the zero-surface.

The computer determines whether the peak intensity is a maximum peak intensity. If the peak intensity is not the maximum peak intensity, the computer adjusts the focusing optics to direct the focal point to a different point of the z-axis.

The computer repeats the following until the peak intensity is a maximum peak intensity: determine whether the peak intensity is a maximum peak intensity; and if the peak intensity is not the maximum peak intensity, adjust the focusing optics to direct the focal point to a different point of the z-axis.

The computer: adjusts the focusing optics to direct the focal point along a plurality of larger intervals to locate a general region of the zero-surface; and adjusts the focusing optics to direct the focal point along a plurality of smaller intervals of the general region to determine the location of the zero-surface.

The computer generates from the signal a graph representing the peak intensity of the reflected portion.

The focusing optics comprise a beam expander, a scanner, and an objective.

The detector optics comprise a polarizer and a quarter-waveplate. The polarizer transmits the laser beam with a first linear polarization to the quarter-waveplate. The quarter-waveplate converts the laser beam from the first linear polarization to a circular polarization, and converts the reflected portion from the circular polarization to a second linear polarization. The polarizer deflects the reflected portion with the second linear polarization towards the TPA detector.

The detector optics comprise a polarizer and a combination comprising a half-waveplate and a Faraday rotator. The polarizer transmits the laser beam with a first linear polarization to the combination. The combination: rotates the linear polarization of the laser beam 0 degrees and rotates the linear polarization of the reflected portion 90 degrees to a second linear polarization; or rotates the linear polarization of the laser beam 90 degrees and rotates the linear polarization of the reflected portion 0 degrees to a second linear polarization. The polarizer deflects the reflected portion with the second linear polarization towards the TPA detector.

BRIEF DESCRIPTION OF THE DRAWINGS

Embodiments of the present disclosure are described by way of example in greater detail with reference to the attached figures, in which.

DESCRIPTION OF EXAMPLE EMBODIMENTS

Referring now to the description and drawings, example embodiments of the disclosed apparatuses, systems, and methods are shown in detail. As apparent to a person of ordinary skill in the field, the disclosed embodiments are exemplary and not exhaustive of all possible embodiments.

Figure 1:
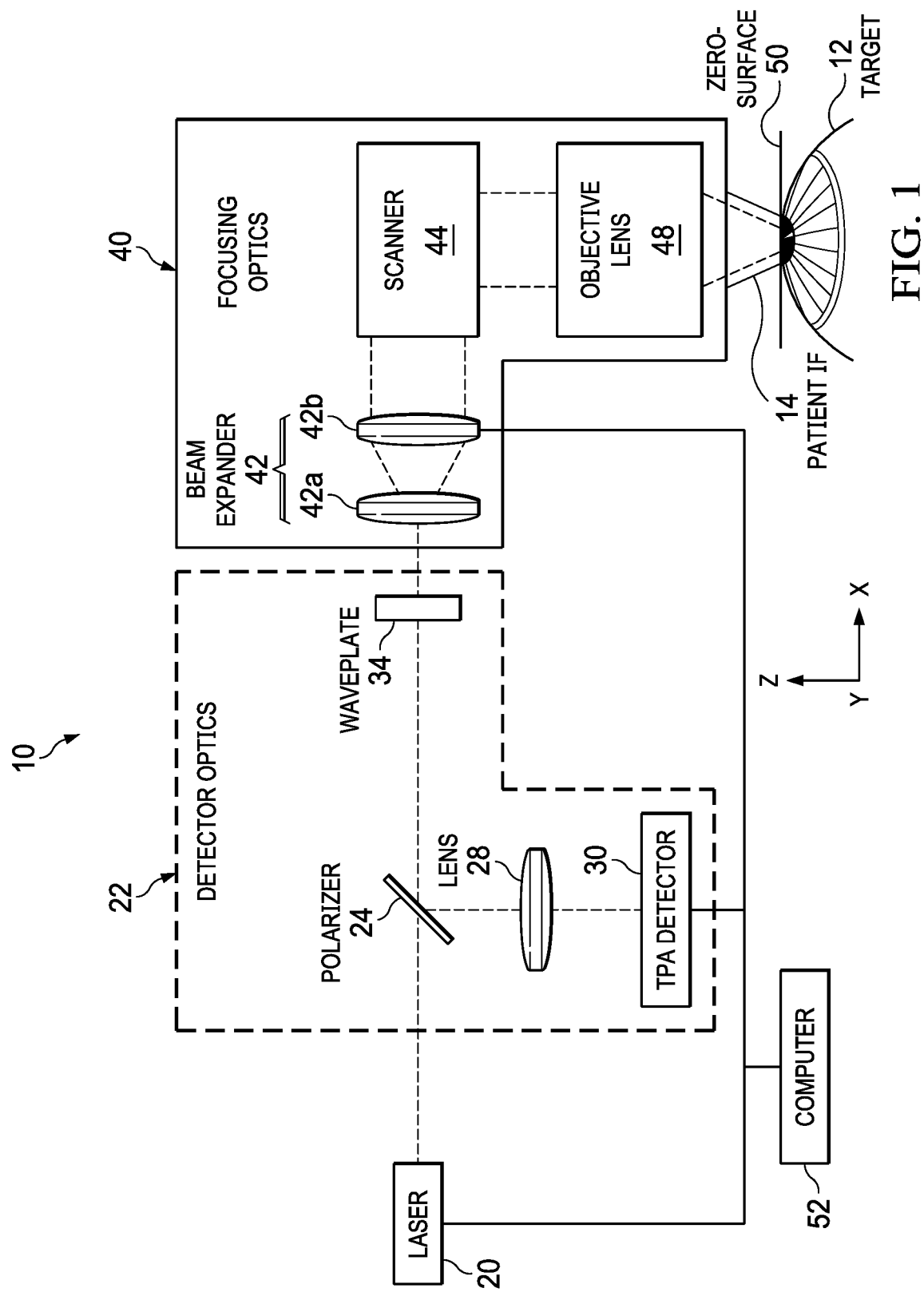
FIG. 1 illustrates an embodiment of a laser system that can calibrate the position of the focal point of a laser beam.

FIG. 1 illustrates an embodiment of a laser system 10 that can calibrate the position of the focal point of a laser beam directed to a target 12, such as an eye or test material. In certain embodiments, a laser generates a laser beam. Focusing optics direct the laser beam to a zero-surface, which may be located generally at the end of a patient IF that stabilizes the eye. The zero-surface reflects at least a portion of the laser beam. Detector optics direct the reflected portion to a two-photon absorption (TPA) detector, which is sensitive to the peak intensity of the reflected portion. In general, when the focal point is at the zero-surface, the diameter of the reflected portion at the detector is at a minimum, and the peak intensity is at a maximum. The peak intensity sensed by the TPA detector indicates the proximity of the focal point of the laser beam to the zero-surface.

In the illustrated embodiment, laser system 10 includes the following coupled as shown: a laser 20, detector optics 22 (including a polarizer 24, a lens 28, and a waveplate 34), a two-photon absorption (TPA) detector 30, focusing optics 40 (including a beam expander 42, a scanner 44, and an objective lens 48), a patient interface 14, and a computer 52. Laser system 10 may be used to perform an ophthalmic procedure on a part of an eye (e.g., the cornea of a human or animal eye) or a test material that mimics that part (e.g., polymethyl methacrylate (PMMA)).

To aid in describing the embodiments, the xyz coordinate system of a laser system is described. The direction of the laser beam as the beam approaches target 12 defines the z-axis. If target 12 is an eye, the z-axis is typically parallel to an optical axis of the eye. The z-axis in turn defines the xy-plane, as the z-axis is normal to the xy-plane. "Z-position" refers to a point of the z-axis; "xy-position" refers to a point of the xy-plane. "Zero-plane" refers to the plane defined by (x, y, z)=(x, y, 0).

Placement of the x- and y-axes on the xy-plane may be selected in any suitable manner. E.g., if target 12 is an eye of a patient, the x- or y- axis may be parallel to a vertical axis of the patient. The origins of the x- and y-axes may be selected in any suitable manner. E.g., if target 12 is an eye, a central portion of the eye (e.g., pupil center, apex, vertex, or optical axis) may define x=0, y=0. The origin of the z-axis, z=0 (which defines the zero-plane) may be selected in any suitable manner. E.g., the target-side surface of interface 14 (i.e., the surface designed to be contact with the eye) may be selected as z=0. During calibration, the target-side surface may or may not actually be in contact with the eye.

To aid in describing the embodiments, optical devices are described. An optical device is a device that controls (e.g., reflects, refracts, filters, transmits (or passes through), and/or polarizes) light. The device can be made of any suitable material that controls the light as designed, e.g., glass, crystal, metal, or semiconductor. Examples of optical devices include lenses, mirrors, prisms, optical filters, waveguides, waveplates, expanders, collimators, splitters, gratings, and polarizers.

Example components of system 10 may be as follows. Laser 20 is a device that generates an intense beam of coherent monochromatic light by stimulated emission of photons from excited atoms or molecules. A laser beam may have any suitable wavelength, e.g., a wavelength in the infrared (IR) or ultraviolet (UV) range. The pulses of the laser beam may have a pulse duration in any suitable range, e.g., the nanosecond, picosecond, femtosecond, or attosecond range. The focus of the laser beam is the focal point of the beam.

Detector optics 22 direct the laser beam to focusing optics 40 and the reflected portion to TPA detector 30. In the illustrated embodiment, detector optics 22 include polarizer 24, lens 28, and waveplate 34. Polarizer 24 is an optical filter that transmits light of a specific polarization direction while reflecting light of other rotated polarization directions. Polarizer 24 can convert light of undefined or mixed polarization into light with a single linear polarization state. In the illustrated embodiment, polarizer 24 transmits the laser beam received from laser 20 (which has a first polarization) towards waveplate 34, and reflects the laser beam received from waveplate 34 (which has a second polarization) towards lens 28 and detector 30. In certain embodiments, the first polarization is a linear polarization, and the second polarization is the linear polarization rotated by 90 degrees. Lens 28 focuses the beam from polarizer 24 to TPA detector, which is located at the focal plane of lens 28. Lens 28 may be an achromatic lens designed to limit the effects of chromatic and spherical aberration.

Waveplate 34 is an optical device that alters the polarization state of a light travelling through it. Waveplate 34 may be any suitable waveplate, e.g., a quarter-waveplate, which converts linearly polarized light into circularly polarized light and vice versa, or a combination of a half-waveplate (which rotates linearly polarized light by 45 degrees) and a 45-degree Faraday rotator (also known as optical diode when used in combination with polarizer 24). In one embodiment, waveplate 34 is a quarter-waveplate that receives the laser beam with a first linear polarization from polarizer 24, converts the laser beam from the first linear polarization to a circular polarization, and directs the laser beam to focusing optics 40. Waveplate 34 also receives the reflected portion of the laser beam from focusing optics 40, and converts the reflected portion from the circular polarization to a second linear polarization rotated relative to first linear polarization. In the illustrated embodiment, waveplate 34 changes the original linear polarization of the light beam by 90 degrees.

In another embodiment, waveplate 34 is a combination of a half-waveplate and a Faraday rotator. Waveplate 34 receives the laser beam with a first linear polarization from polarizer 24. In this direction, the half-waveplate and Faraday rotator compensate for each other's rotational effect, resulting in rotation of the laser beam by 0 degrees. Waveplate 34 then directs the laser beam to focusing optics 40. Waveplate 34 also receives the reflected portion of the laser beam reflected from focusing optics 40. In this direction, the half-waveplate and Faraday rotator add their rotational effects, resulting in rotation of the laser beam by 90 degrees, which is a second linear polarization rotated relative to the first linear polarization. In summary, the light beam passes through waveplate 34, which rotates the beam by 0 degrees, and is reflected back through waveplate 34, which rotates the beam by 90 degrees, resulting in a change from the original linear polarization of the light beam by 90 degrees. In other embodiments, waveplate 34 may be reconfigured such that the light beam passes through waveplate 34, which rotates the beam by 90 degrees, and is reflected back through waveplate 34, which rotates the beam by 0 degrees.

Focusing optics 40 direct and focus the laser beam towards target 12. In certain embodiments, focusing optics 40 direct the focal point of the laser beam along the z-axis towards a zero-surface 50 and receive at least a portion of the beam reflected by zero-surface 50. In the illustrated embodiment, focusing optics 40 include beam expander 42, scanner 44, and objective lens 48. Beam expander 42 includes one or more optical devices that expand the diameter of a laser beam to control the focal point of a laser beam. An optical device, such as a lens 42a or a mirror, may control the z-position of the focal point of a laser beam, and another optical device, such as a lens 42b (in combination with lens 42a), may expand the diameter of a laser beam. In theory, beam expander 42 is designed to consistently control the focal point of a laser beam. However, in practice, the optics may vary over time such that the z-position of the focal point changes. Accordingly, in certain cases, calibration of the z-position of the focal point of the laser beam may be important.

Scanner 44 includes one or more optical devices that control the direction of a laser beam to control the xy-position of the focal point. To transversely deflect the laser beam, scanner 44 may have a pair of galvanometric actuated scanner mirrors that tilt about mutually perpendicular axes. In the illustrated embodiment, scanner 44 receives the laser beam from the beam expander 42, and manipulates the laser beam to control the xy-position of the focal point. Objective lens 48 receives the laser beam from the scanner 44 and directs the beam to target 12.

Patient interface (IF) 14 stabilizes the position of target 12 relative to laser system 10 during surgery, and is typically made of a rigid material such as plastic or metal. If target 12 is an eye, contact between the eye and certain types of patient IFs 14 may shape (e.g., flatten or otherwise deform) the surface of the eye. The "target-side" surface of patient IF 14 is the surface of IF 14 designed to face (and may even be in contact with) target 12. Patient IFs 14 are typically one-time-use products, where one IF 14 is used for one patient eye and then discarded. In theory, patient IFs 14 are designed to have a consistent length in the z-direction. However, in practice, different IFs may have different lengths. Accordingly, in certain cases, calibration of the z-position of the focal point with respect to a particular patient IF 14 is important.

In certain embodiments, the target-side surface of patient IF 14 defines z=0, or the zero-plane. A zero-surface 50, which reflects the laser beam during calibration, may be located at the zero-plane. Examples of zero-surface 50 includes the target-side surface of patient IF 14, the other side of the target-side surface, or another surface (e.g. a mirrored or other highly reflective surface), placed close to or in contact with the target-side surface of patient IF 14. Please note that while FIG. 1 illustrates target 12 and zero-surface 50, in practice, target 12 is typically not present when calibration is being conducted.

Two-photon absorption (TPA) detector 30 measures the intensity of a laser beam. In certain detectors, the laser beam causes two-photon absorption that excites electrons, which generate a signal in response to the peak intensity of the incident radiation. In the illustrated embodiment, TPA detector 30 senses the intensity of the reflected portion, and generates a signal indicating the peak intensity of the reflected and focused portion.

The signal indicates the proximity of the focal point of the laser beam to zero-surface 50. The farther away the focal point is from zero-surface 50, the larger the diameter of the reflected portion on the sensing surface of the TPA detector, and the lower the peak intensity of the beam at a particular portion of the detector. The closer the focal point is to zero-surface 50, the smaller the diameter of the reflected portion, and the higher the peak intensity of the beam at a particular portion of the detector. Accordingly, when the focal point is at zero-surface 50, the diameter at the detector is a minimum, and the peak intensity is at a maximum.

Computer 46 determines whether the focal point of the laser beam is calibrated in response to intensity measurements from TPA detector 30. In certain embodiments, computer 46 determines whether the peak intensity is a maximum peak intensity. The maximum peak intensity may be the maximum of peak intensities measured at different positions of the focal point. In some cases, the maximum peak intensity may be measured or calculated prior to a calibration session, so computer 46 can determine if the peak intensity measured during the calibration session is at a maximum. If the peak intensity is the maximum peak intensity, computer 46 determines that the focal point is at zero-surface 50. If the peak intensity is not the maximum peak intensity, computer 46 may adjust focusing optics 40 to direct the focal point to a different point of the z-axis. Adjusting focusing optics 40 is described in more detail with reference to FIG. 2. In certain embodiments, computer 46 generates from the TPA detector signal a graph representing the peak intensities of the reflected portion. Examples of graphs are described in more detail with references to FIGS. 3, 4A, and 4B.

Figure 2:
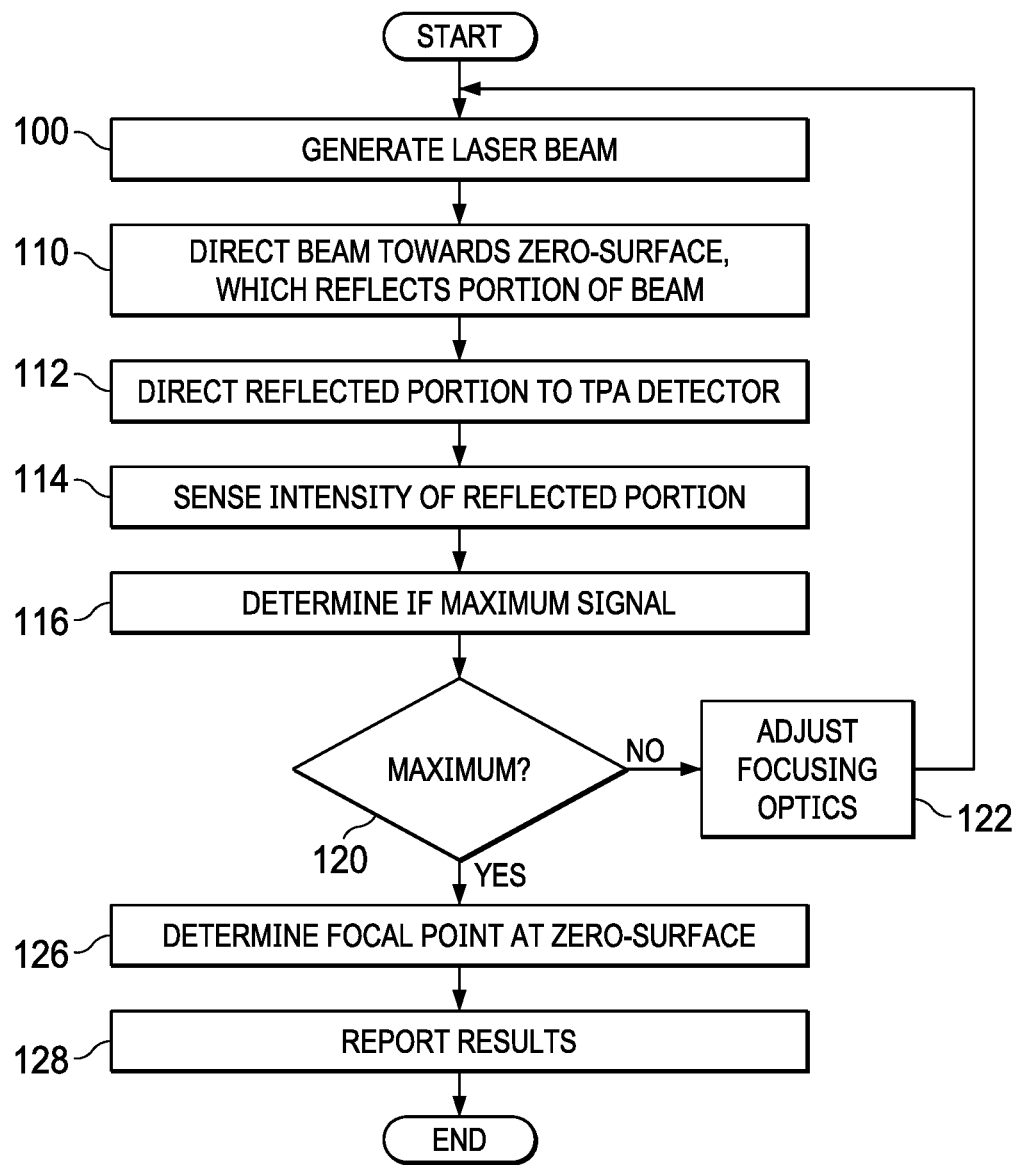
FIG. 2 illustrates an example of a method that may be performed by the system of FIG. 1 to calibrate a focal point of a laser beam.

FIG. 2 illustrates an example of a method that may be performed by system 10 of FIG. 1 to calibrate a focal point of a laser beam. The method starts at step 100, where laser 20 generates a laser beam. Focusing optics 40 direct the laser beam to zero-surface 50 at step 110, which reflects at least a portion of the laser beam. The remainder of the beam may travel to target 12. Detector optics 22 direct the reflected portion to TPA detector 30 at step 112. TPA detector 30 detects the intensity of the reflected portion at step 114.

Computer 46 determines if the peak intensity is the maximum peak intensity by determining if the signal is at a maximum at step 116. If the signal is not at a maximum at step 120, computer 46 may adjust focusing optics 40 at step 122 to direct the focal point to a different point of the z-axis. For example, computer 46 may instruct focusing optics 40 to change the position or refractive properties of lens 42a to adjust the position of the focal point. The adjustments may follow one or more prescribed patterns to move the focal point towards zero-surface 50. An example is described with reference to FIG. 3.

Figure 3:
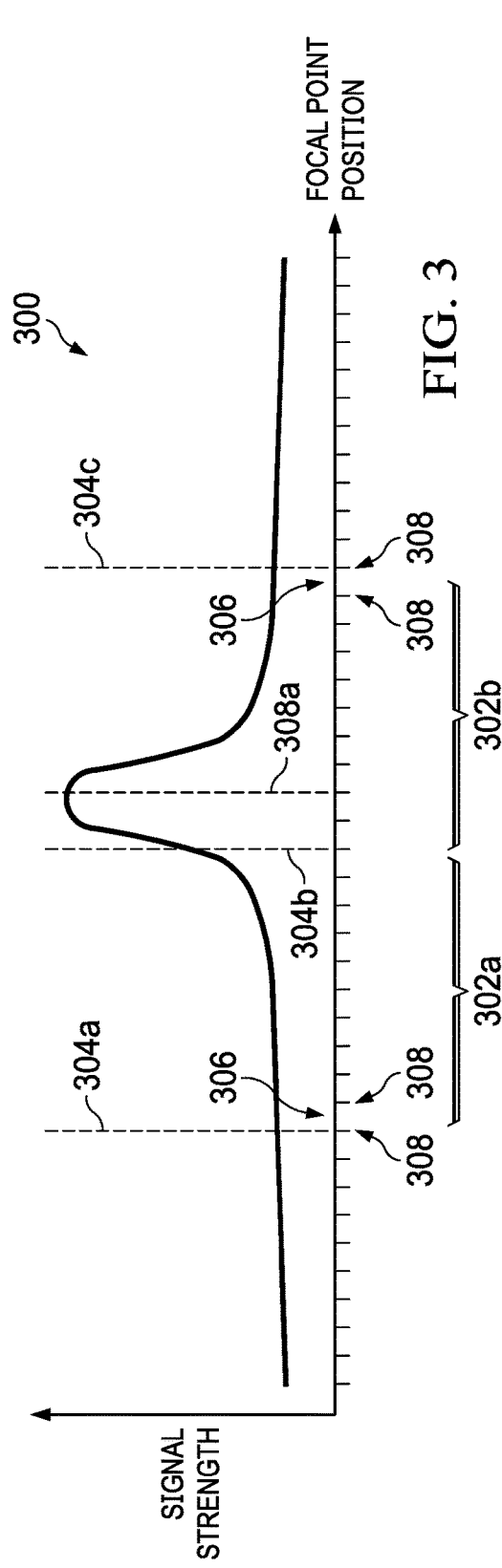
FIG. 3 is a graph that illustrates an example of an adjustment pattern that may be performed by the system of FIG. 1.

FIG. 3 is a graph 300 that illustrates an example of an adjustment pattern. The vertical axis of graph 300 represents the TPA signal (measured in, e.g., volts V or amperes A), which indicates the peak intensity, and the horizontal axis represents the position of the focal point (measured in, e.g., micrometers μm or otherwise indicated by laser system 10). In the example, computer 46 instructs focusing optics 40 to first adjust the position of the focal point at larger intervals 302, defined by positions 304 (304a-c) to locate the general region of zero-surface 50. The general region may be, e.g., the larger intervals 302 greater and less than the position 304 with the highest signal measured at the positions 304. Larger intervals 302 may have any suitable size. In certain cases, the size may be selected in light of the manufacturing tolerance of patient IF 14, e.g., the size may be 0.5 to 1.5, 1.5 to 2.5, or 2.5 to 3.5 times greater than the manufacturing tolerance. For example, if the manufacturing tolerance is <25 μm, the size may be selected as 50 μm. According to graph 300, the TPA signal is highest at position 304b, so the general region of zero-surface 50 may be the interval 302b greater than 304b and the interval 302a less than 304b.

Computer 46 then instructs focusing optics 40 to adjust the position at smaller intervals 306, defined by positions 308, within the general region to narrow down the position of the maximum signal, which indicates the location of zero-surface 50. Smaller intervals 306 may have any suitable size. In certain cases, the size may be selected in light of the size of larger intervals 302, e.g., the size of smaller intervals 306 may be 0.001 to 0.01 or 0.01 to 0.1 of the size of larger intervals 302. For example, if the size of larger intervals 302 is 50 μm, the size of smaller intervals 306 may be selected as 1 μm. According to graph 300, the signal at position 308a is between rising and falling parts of the signal, i.e., the maximum signal, is estimated around position 308a, so the zero-surface 50 may be substantially at position 308a. "Substantially at" may be described as within the smaller intervals 306 about position 308a. In certain embodiments, interpolation may be performed to further refine the position of zero-surface 50.

Referring back to FIG. 2, as another example of an adjustment pattern that may be performed at step 122, computer 46 may instruct focusing optics 40 to change the position or refractive properties lens 42a to move the focal point in one direction. If movement in that direction increases the signal, indicating the focal point is moving closer to zero-surface 50, movement may continue in that direction until the maximum signal is reached. If movement in that direction decreases the signal, indicating the focal point is moving farther away from to zero-surface 50, movement of the focal point may be changed to the opposite direction.

If the signal is at a maximum at step 120, computer 46 determines that the focal point is substantially at zero-surface 50 at step 126 and reports the results at step 128. In certain embodiments, interpolation may be performed to further refine the position of zero-surface 50. The method then ends.

Figure 4A:
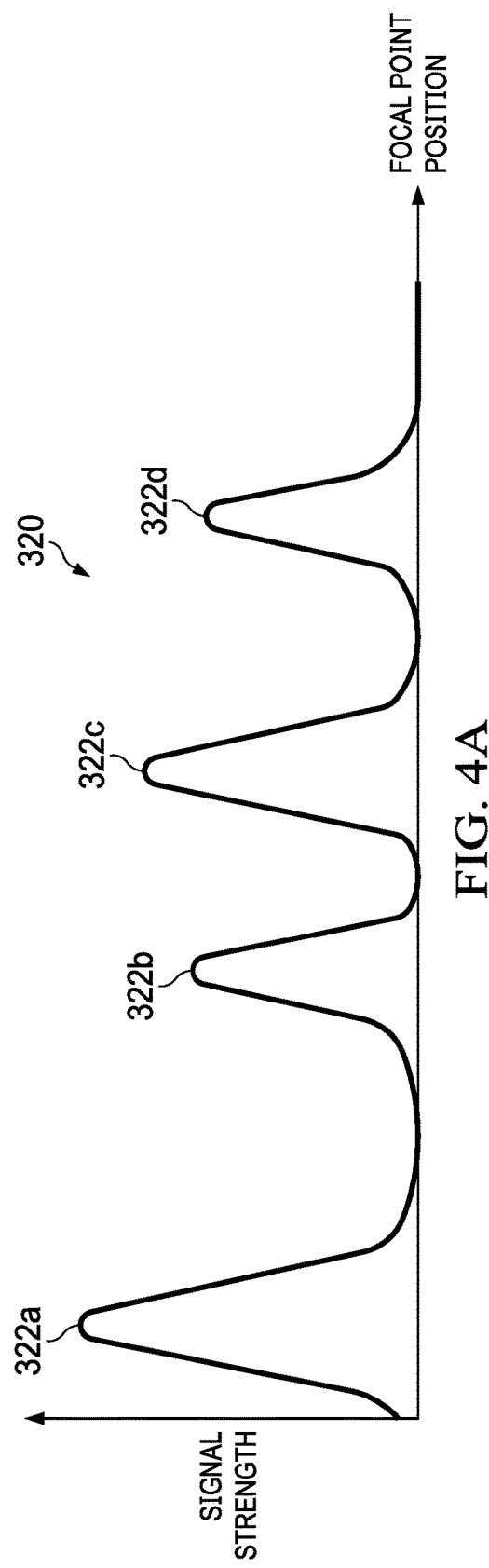
FIGS. 4A and 4B are graphs that illustrate examples of calibrating the laser beam for patient IFs of different lengths that may be performed by the system of FIG. 1.
Figure 4B:
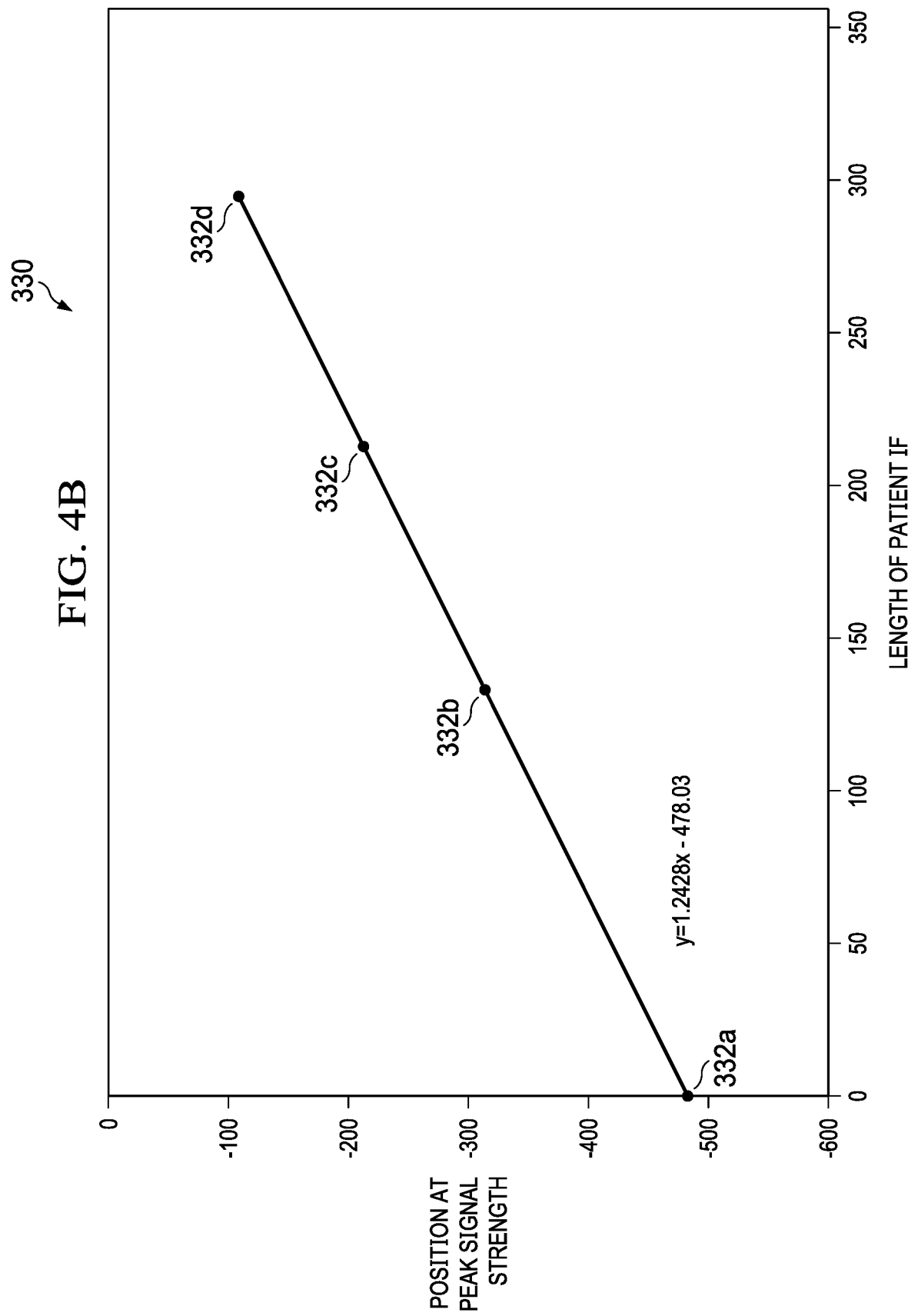

FIGS. 4A and 4B are graphs 320 and 330 that illustrate examples of calibrating the laser beam for patient IFs 14 of different lengths. Computer 52 of system 10 of FIG. 1 may generate graphs 320 and 330. The units of measure may be as described in previous graphs, unless otherwise noted.

FIG. 4A is a graph 320 that illustrates an example of the TPA signal patterns of patient IFs 14 of different lengths. The vertical axis of graph 300 represents the TPA signals, which indicate peak intensities, and the horizontal axis represents the position of the focal point. Peaks 322a-d represent the positions of the maximum signal for patient IFs 14 of different lengths. Peaks 322a-d occur at different focal point positions, as they should for patient IFs 14 of different lengths.

FIG. 4B is a graph 330 that illustrates the focal point positions of the maximum signal of patient IFs 14 of different lengths. The vertical axis of graph 300 represents the focal point position of the maximum peak intensity, and the horizontal axis represents the length of the patient IF 14 (measured in, e.g., μm). Graph 300 shows the focal point position and the length of the patient IF 14 are linearly related.

A component (e.g., a computer) of the systems and apparatuses disclosed herein may include an interface, logic, and/or memory, any of which may include hardware and/or software. An interface can receive input to the component, provide output from the component, and/or process the input and/or output. Logic can perform the operations of the component, e.g., execute instructions to generate output from input. Logic may be a processor, such as one or more computers or one or more microprocessors (e.g., a chip that resides in computers such as a field-programmable gate array (FPGA)). Logic may be computer-executable instructions encoded in memory that can be executed by a computer, such as a computer program or software. A memory can store information and may comprise one or more tangible, non-transitory, computer-readable, computer-executable storage media. Examples of memory include computer memory (e.g., Random Access Memory (RAM) or Read Only Memory (ROM)), mass storage media (e.g., a hard disk), removable storage media (e.g., a Compact Disk (CD) or a Digital Video Disk (DVD)), and network storage (e.g., a server or database).

Although this disclosure has been described in terms of certain embodiments, modifications (such as substitutions, additions, alterations, or omissions) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, and the operations of the systems and apparatuses may be performed by more, fewer, or other components. As another example, modifications may be made to the methods disclosed herein. The methods may include more, fewer, or other steps, and the steps may be performed in any suitable order.

What is claimed is:

1. A system for calibrating a position of a focal point of a laser beam, comprising:
   a laser configured to generate the laser beam;
   a plurality of focusing optics configured to:
      direct the focal point of the laser beam along a z-axis towards a zero-surface, the zero-surface corresponding to a zero-plane; and
      receive at least a portion of the laser beam reflected by the zero-surface;
   one or more detector optics configured to:
      receive the reflected portion from the focusing optics; and
      direct the reflected portion towards a two-photon absorption (TPA) detector;
   the TPA detector configured to:
      sense a peak intensity of the reflected portion, the peak intensity indicating a proximity of the position of the focal point of the laser beam to the zero-surface; and
      generate a signal representing the peak intensity of the reflected portion; and
   a computer configured to determine whether the position of the focal point of the laser beam is calibrated in response to the signal representing the peak intensity.

2. The system of claim 1, the computer configured to:
   determine whether the peak intensity is a maximum peak intensity; and
   if the peak intensity is the maximum peak intensity, determine that the position of the focal point of the laser beam is substantially at the zero-surface.

3. The system of claim 1, the computer configured to:
   determine whether the peak intensity is a maximum peak intensity; and
   if the peak intensity is not the maximum peak intensity, adjust the plurality of focusing optics to direct the focal point of the laser beam to a different point of the z-axis.

4. The system of claim 1, the computer configured to repeat the following until the peak intensity is a maximum peak intensity:
   determine whether the peak intensity is a maximum peak intensity; and
   if the peak intensity is not the maximum peak intensity, adjust the plurality of focusing optics to direct the focal point of the laser beam to a different point of the z-axis.

5. The system of claim 1, the computer configured to:
adjust the plurality of focusing optics to direct the focal point of the laser beam along a plurality of larger intervals to locate a general region of the zero-surface; and
adjust the plurality of focusing optics to direct the focal point of the laser beam along a plurality of smaller intervals of the general region to determine the location of the zero-surface.

6. The system of claim 1, the computer configured to:
generate from the signal a graph representing the peak intensity of the reflected portion.

7. The system of claim 1, the plurality of focusing optics comprising a beam expander, a scanner, and an objective.

8. The system of claim 1, wherein the one or more detector optics comprise a polarizer and a quarter-waveplate:
the polarizer configured to transmit the laser beam with a first linear polarization to the quarter-waveplate;
the quarter-waveplate configured to:
convert the laser beam from the first linear polarization to a circular polarization; and
convert the reflected portion from the circular polarization to a second linear polarization;
the polarizer further configured to deflect the reflected portion with the second linear polarization towards the TPA detector.

9. The system of claim 1, wherein the one or more detector optics comprise a polarizer and a combination comprising a half-waveplate and a Faraday rotator:
the polarizer configured to transmit the laser beam with a first linear polarization to the combination;
the combination configured to:
rotate the linear polarization of the laser beam 0 degrees and rotate the first linear polarization of the reflected portion 90 degrees to a second linear polarization; or
rotate the linear polarization of the laser beam 90 degrees and rotate the first linear polarization of the reflected portion 0 degrees to a second linear polarization; and
the polarizer further configured to deflect the reflected portion with the second linear polarization towards the TPA detector.

10. A method for calibrating a position of a focal point of a laser beam, comprising:
generating a laser beam;
directing, by a plurality of focusing optics, the focal point of the laser beam along a z-axis towards a zero-surface, the zero-surface corresponding to a zero-plane;
receiving at least a portion of the laser beam reflected by the zero-surface;
receiving, by one or more detector optics, the reflected portion from the focusing optics;
directing the reflected portion towards a two-photon absorption (TPA) detector;
sensing, by the TPA detector, a peak intensity of the reflected portion, the peak intensity indicating a proximity of the position of the focal point of the laser beam to the zero-surface;
generating a signal representing the peak intensity of the reflected portion; and
determining, by a computer, whether the position of the focal point of the laser beam is calibrated in response to the signal representing the peak intensity.

11. The method of claim 10, further comprising:
determining, by the computer, whether the peak intensity is a maximum peak intensity; and
when the peak intensity is the maximum peak intensity, determining that the position of the focal point of the laser beam is substantially at the zero-surface.

12. The method of claim 10, further comprising:
determining, by the computer, whether the peak intensity is a maximum peak intensity; and
when the peak intensity is not the maximum peak intensity, adjusting the plurality of focusing optics to direct the focal point of the laser beam to a different point of the z-axis.

13. The method of claim 10, further comprising repeating, by the computer, the following until the peak intensity is a maximum peak intensity:
determining whether the peak intensity is a maximum peak intensity; and
when the peak intensity is not the maximum peak intensity, adjusting the plurality of focusing optics to direct the focal point of the laser beam to a different point of the z-axis.

14. The method of claim 10, further comprising:
adjusting, by the computer, the plurality of focusing optics to direct the focal point along a plurality of larger intervals to locate a general region of the zero-surface; and
adjusting the plurality of focusing optics to direct the focal point of the laser beam along a plurality of smaller intervals of the general region to determine the location of the zero-surface.

15. The method of claim 10, the computer configured to:
generating, by the computer, from the signal a graph representing the peak intensity of the reflected portion.

* * * * *